United States Patent [19]
Dohnalek et al.

[11] Patent Number: 5,827,526
[45] Date of Patent: Oct. 27, 1998

[54] USE OF INDIGESTIBLE OLIGOSACCHARIDES TO PREVENT GASTROINTESTINAL INFECTIONS AND REDUCE DURATION OF DIARRHEA IN HUMANS

[75] Inventors: Margaret Ione Halpin Dohnalek, Worthington; Karin Margaret Ostrom, Reynoldsburg; Milo Duane Hilty, Lewis Center, all of Ohio

[73] Assignee: Abbott Laboratories, Abbott Park, Ill.

[21] Appl. No.: 653,084

[22] Filed: Jun. 12, 1996

Related U.S. Application Data

[60] Provisional application No. 60/001,036 Jul. 11, 1995.
[51] Int. Cl.$^6$ .................................................... A61K 9/68
[52] U.S. Cl. .................. 424/440; 424/439; 424/197.11; 424/195.1; 424/73; 514/867; 514/54
[58] Field of Search ........................... 424/197.11, 195.1, 424/73, 440, 439; 514/867, 54

[56] References Cited

U.S. PATENT DOCUMENTS

| | | | |
|---|---|---|---|
| 4,859,488 | 8/1989 | Kan | 426/658 |
| 4,873,229 | 10/1989 | Deya et al. | 514/54 |
| 4,987,124 | 1/1991 | Speights et al. | 514/23 |
| 5,219,842 | 6/1993 | Okada et al. | 514/54 |
| 5,437,880 | 8/1995 | Takaichi et al. | 426/73 |
| 5,444,054 | 8/1995 | Garleb et al. | 514/54 |

FOREIGN PATENT DOCUMENTS

| | | |
|---|---|---|
| 0 293 935 A | 12/1988 | European Pat. Off. . |
| 0 549 478 A | 6/1993 | European Pat. Off. . |
| WO 94 27618 A | 12/1994 | WIPO . |

OTHER PUBLICATIONS

Patent Abstracts of Japan, vol. 9, No. 287 (C–314), 14 Nov. 1985 and JP 60 133852 A (Zenkoku Shiyokubutsu Tanpaku Shiyokuhin Kiyoudoukumiai), 17 Jul. 1985; See abstract.

Faseb Journal, vol. 9, No. 3, 1995, p. A368 XP002025324, Chandra, G. et al.: "The addition of neosugar to oral electrolyte solutions (OES) for treatment of acute diarrhea", See Abstract.

Patent Abstracts of Japan, vol. 17, No. 670 (C–1139), 9 Dec. 1993 and JP 05 219897 A (Ajinomoto Co. Inc.), 31 Aug. 1993, See Abstract.

Database WPI, Week 8915, Derwent Publications Ltd., London, GB; AN 89–109964 XP002025325 & JP 01 055 150 A (Suntory Ltd.), 2 Mar. 1989, See Abstract.

*Primary Examiner*—Thurman K. Page
*Assistant Examiner*—D. Faulkner
*Attorney, Agent, or Firm*—Thomas D. Brainard; J. Michael Dixon

[57] ABSTRACT

A method is provided for reducing the duration of diarrhea and recurrent episodes of diarrhea in humans by enterally administering indigestible oligosaccharides prophylactically. More specifically, the present invention relates to a method using indigestible oligosaccharides or fructooligosaccharides (FOS) to reduce the duration and recurrence of diarrhea in a human wherein between 0.5 grams and 5 grams of at least one FOS selected from the group consisting of 1-kestose, nystose, and $1^F$-β-fructofuranosyl nystose is administered to said human per day. The indigestible oligosaccharides can be produced through enzymatic synthesis, chemical techniques or isolated from plant materials and are administered in the form of a nutritional product, candy, tablets, chewing gum, lozenges, milk, yogurts, fermented products and the like.

8 Claims, No Drawings

USE OF INDIGESTIBLE OLIGOSACCHARIDES TO PREVENT GASTROINTESTINAL INFECTIONS AND REDUCE DURATION OF DIARRHEA IN HUMANS

This application claims the benefit of U.S. Provisional Application No. 60/001,036, filed Jul. 11, 1995.

FIELD OF THE INVENTION

The present invention relates to a method of reducing duration of diarrhea by enterally administering to humans indigestible oligosaccharides.

BACKGROUND OF THE INVENTION

Prevention of gastrointestinal infections in young children and in adults is a significant public health problem that has not been solved. Methods of prevention presently available are limited to practices that reduce transmission of infectious agents to susceptible individuals. Such methods include sewage treatment, provisions of clean water, hand washing, and good personal hygiene. The development of effective vaccines to prevent colonization by enteric pathogens has been limited due to the large number of potential pathogens and because young children, who are at greatest risk, fail to develop long-lasting immunity. Individuals treated with antibiotics for infectious diseases may also become colonized with antibiotic-resistant bacteria and may not respond to antibiotic treatment at a later time.

Fructooligosaccharides (FOS) are natural substances composes primarily of fructose molecules. They belong to a group of carbohydrates that occur in many different plants. FOS are indigestible oligosaccharides that pass through the small intestine without being digested, reaching the large intestine where they are selectively fermented by certain microorganisms. As used in this application and the claims, the terms FOS and indigestible oligosaccharides are interchangeable. FOS can be utilized efficiently by lactobacilli and bifidobacteria, species of bacteria that are beneficial for human health (Hidaka et al.). Selective fermentation of FOS by bifidobacteria leads to an increase in the presence of these bacteria and to the production of acetic acid and lactic acid as fermentation endproducts, resulting in a lower pH in the digestive tract and providing a means to prevent the overgrowth of harmful bacterial like *Escherichia coli*, *Clostridium perfringens* and *Clostridium difficile*. (Hidaka et al., "Fructooligosaccharides: Enzymatic Preparation and Biofunctions", *Journal of Carbohydrate Chemistry* 10(4): 509–522, 1991). Fermentation of FOS can also lead to an increase in the presence of short chain fatty acids and the suppression of undesirable microorganisms such as *Clostridium perfringens, C. difficile,* or *E. coli* and the toxins they produce (Hidaka et al. "Fructooligosaccharides: Enzymatic Preparation and Biofunctions", *Journal of Carbohydrate Chemistry* 10(4): 509–522, 1991). Indigestible oligosaccharides such as FOS can be added to a nutritional product to create an environment in the gastrointestinal tract that is not conducive to the growth of microbial pathogens. Such a nutritional product can also be useful in the prevention of diarrhea caused by these pathogens.

Indigestible Oligosaccharides

"Indigestible oligosaccharides" refers to a small carbohydrate moiety that is resistant to endogenous digestion in the human upper digestive tract. Fructooligosaccharides (FOS) are indigestible oligosaccharides that are members of the inulin subclass of fructosans, polymers composed of fructose residues. FOS are sometimes characterized by their degree of polymerization. Degree of polymerization (DP) means the number of covalent bonds between the monosaccharide units in the polymer. For example, the tetramer nystose is composed of three fructose monomers bound to glucose (or sucrose plus two fructose units) and has a DP of 3. Using this nomenclature, sucrose is $GF_1$ (glucose plus fructose). Specifically, inulins are glucofructosans, carbohydrate polymers consisting of a chain of fructose residues linked by $(2\rightarrow1)$-$\beta$-glycosidic bonds and usually having a single D-glycosyl residue lined $(1\rightarrow2)$-$\alpha$-to the first fructose molecule.

Fructooligosaccharides (FOS) can be produced enzymatically through chemical techniques or by extraction from natural substances. FOS occur in nature in many kinds of plants, including onions, garlic, shallots, artichokes, wheat, rye, bananas, asparagus and tomatoes, that are commonly part of a human diet (Speights et al., "Fructooligosaccharides—A Low Caloric Bulking Agent And More From Sucrose", *Carbohydrates in Industrial Synthesis*, ed. M. A. Clarke, Proceedings of the Symposium of the Division of Carbohydrate Chemistry of the American Chemical Society, 1992). Another natural source of FOS is the chicory root. FOS can also be synthesized from sucrose through the use of transfructosylating enzymes. Treatment of sucrose with the transfructosylating enzyme from *Aspergillus niger* results in a mixture of fructooligosaccharides containing 2, 3 or 4 fructose residues, designated respectively: 1-kestose or $GF_2$ in which one molecule of fructose is bound to sucrose; nystose or $GF_3$ in which two molecules of fructose are bound to sucrose; and $1^F$-$\beta$-fructofuranosyl nystose or $GF_4$ in which three molecules of fructose are bound to sucrose.

An enzymatic method of producing FOS industrially is taught in U.S. Pat. No. 4,681,771 to Adachi et al. that comprises reacting sucrose in the presence of a fructosyltransferase (enzyme) to obtain $GF_2$, $GF_3$, $GF_4$ and $GF_5$. The source for the enzyme, fructosyltransferase, could be a fungus such as *Aspergillus niger.*

Richards (U.S. Pat. No. 5,318,794) discloses a method for producing a product (caramel) containing between 20 and 50% fructooligosaccharides, having a degree of polymerization (DP) of about 3–10. The method comprises heating sucrose and an organic acid until fructose oligosaccharides are formed. This method produces a mixture of oligosaccharides, many of which differ in structure from the $GF_2$, $GF_3$ and $GF_4$ used in the present invention.

Richards et al. (WO 94/27618) discloses a method for the treatment and prevention of diarrhea comprising administration of a caramel prepared according to U.S. Pat. No. 5,318,794 or U.S. Pat. No. 5,206,355. These patents disclose a method for the preparation of trisaccharides and a fructoglucan sucrose polymer. WO 94/27618 provides examples of infants and adults suffering from diarrhea who were treated with the caramels. The present invention is, by contrast, directed to a method for decreasing the duration of diarrhea episodes by the administration of products containing the fructooligosaccharides $GF_2$, $GF_3$ and $GF_4$. WO 94/27618 claims a method for treatment or prevention of diarrhea, but only gives examples of treatment. The present invention relates to prophylactic use of FOS to shorten duration of diarrhea.

Analysis of human breast milk has determined that it does not contain the FOS useful in this invention. Kunz and Rudloff have reported in an article entitled "Biological Functions of Oligosaccharides in Human Milk", Acta Paediatr. 82:903–12 (1993) that the monomers of breast milk oligosaccharides are D-glucose, D-galactose, N-acetylglucosamine, L-fucose and sialic acid. With few exceptions, all of the breast milk oligosaccharides carry lactose at their reducing end. In contrast, the present inventors have discovered that the very different fructooligosaccharides (FOS) with a degree of polymerization of from 2 to 20, can reduce the manifestation of diarrhea in a human consuming from 0.5 to 5 grams per day FOS.

FOS are not hydrolyzed in the small intestine by human digestive enzymes and thus reach the large intestine intact. There, many intestinal microorganisms utilize them. FOS can be utilized most efficiently by bifidobacteria, which are believed to be highly beneficial organisms (Hidaka, et al.), but cannot be utilized by certain undesirable, such as *E. coli* and putrefactive bacteria such as *Clostridium perfringens* or *Clostridium difficile*.

Carbohydrates which are not digested in the small intestine can be fermented to short chain fatty acids by the microorganisms found in the large intestine. The selective utilization by intestinal bacteria leads to an increase in the presence of bifidobacteria, the production of short chain fatty acids, lowered pH in the large intestine, and the suppression of undesirable microorganisms and the toxins they produce (Hidaka et al.).

Animal toxicology studies have shown no evidence of toxicity, mutagenicity, or carcinogenic effects due to FOS (Clevenger et al., "Toxicological evaluation of neosugar: genotoxicity, carcinogenicity, and chronic toxicity", *Journal of the American College of Toxicology* 7:643–662, 1988). FOS is used in Japan in many food products and has been added to infant formula (Fructooligosaccharide Information Package, Coors BioTech, Inc. May 1990).

SUMMARY OF THE INVENTION

There is disclosed a method for reducing the duration of diarrhea and the number of recurrent episodes of diarrhea in a human, said method comprises enterally administering a therapeutically effective amount of an indigestible oligosaccharide to said human prior to an incident of diarrhea.

More specifically, the method of the present invention is accomplished through the administration of at least one indigestible oligosaccharide selected from fructooligosaccharide, fructosans, xylooligosaccharides and galactooligosaccharides. More preferably, the fructooligosaccharide is selected from 1-kestose, nystose and $1^F$-$\beta$-fructofuranosyl nystose.

In the method of this invention, the indigestible oligosaccharide can be administered in the form of candy, chewing gum, tablets, lozenges or a nutritional product. For the treatment of infants, the indigestible oligosaccharide may be incorporated into an infant formula. The present invention can also be accomplished through incorporating the oligosaccharides, useful in this method, in follow-on formula, toddler's beverages, yogurts, milks, fruit juice, fruit-based drinks, dietary supplements and the like. One aspect of this invention relates to the discovery that the indigestible oligosaccharide is administered to a human at a rate between 0.5 grams per day and 5 grams per day prior to the onset of diarrhea. In a more preferred embodiment, the human consumes 1.0 to 4.0 grams per day and in yet a still more preferred embodiment, the human consumes 1.5 to 3.5 grams per day of FOS.

In order to demonstrate the present invention, a clinical study was undertaken testing whether the enteral administration of FOS would reduce the incidence and/or duration of diarrhea.

A 16 week, controlled, randomized, blinded study was undertaken to determine if prophylactic feeding of fructooligosaccharides or indigestible oligosaccharides can reduce the incidence and shorten the duration of diarrhea in young children. Children between the ages of 10 and 24 months were randomly assigned to receive either a milk-based beverage which served as a control, or the same beverage supplemented with FOS.

DETAILED DESCRIPTION OF THE INVENTION

As used herein and in the claims, "indigestible oligosaccharides" refers to carbohydrates with a degree of polymerization of from 2 to 20 ($GF_2$–$GF_{20}$) and/or a molecular weight less than about 3,600 that is resistant to endogenous digestion in the human upper digestive tract. These "indigestible oligosaccharides" are utilized as a substrate for fermentation by selected bacteria like lactobacilli and bifidobacteria species and other nonpathogenic bacteria that reside in the lower gastrointestinal tract. Indigestible oligosaccharides that may be employed in the invention may be prepared enzymatically, prepared by chemical means or extracted from natural products. As used herein and the claims, a therapeutically effective amount of the indigestible oligosaccharides can range from 0.5–5 grams per day.

Chemical structures of sucrose and some fructooligosaccharides useful in the practice of the present invention are shown below. The general structural formula is shown as $GF_n$ and the fructosan molecule is designated $F_m$. Any molecule depicted as $GF_n$ or $F_m$ can be used in the practice of the present invention provided that $n$ and $m$ are between 2 and 20. These include in the preferred embodiment 1-kestose ($GF_2$ in which one molecule of fructose is bound to sucrose), nystose ($GF_3$ in which two molecules of fructose are bound to sucrose), and $1^F$-$\beta$-fructofuranosyl nystose ($GF_4$ in which three molecules of fructose are bound to sucrose). In other embodiments of the invention, indigestible oligosaccharides such as xylooligosaccharides and galactooligosaccharides having a degree of polymerization ranging from 2 to 20 are also useful. Xylooligosaccharides selected from the group consisting of xylobiose, xylotriose and xylotetrose are useful in this invention. Galactooligosaccharides [(Galactose)$_N$-Galactose-Glucose], where N can range from 1 to 10 are also useful in the present invention.

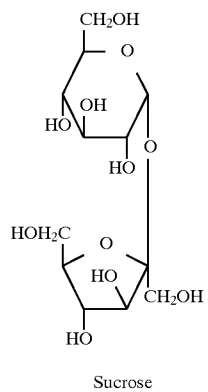

Sucrose

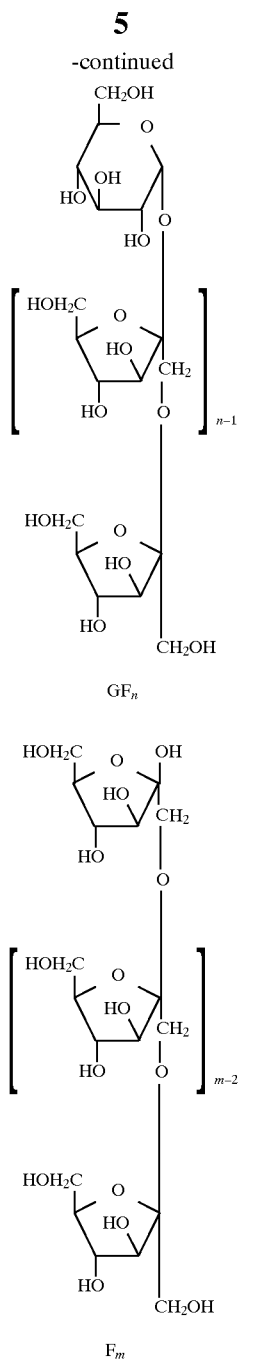
GF$_n$
F$_m$
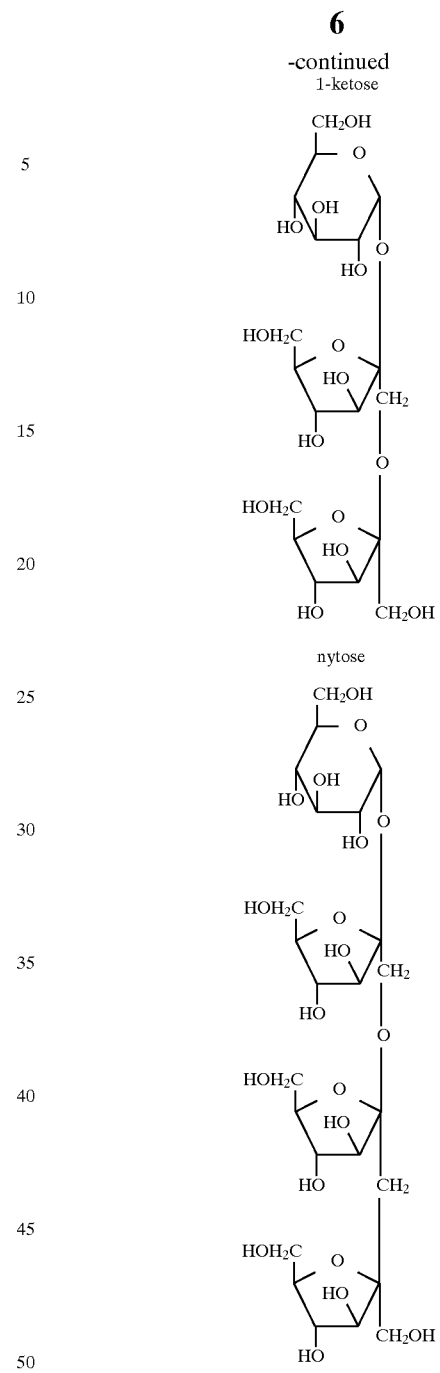
1-ketose
nytose

-continued

1^F-βfructo-furanosyl

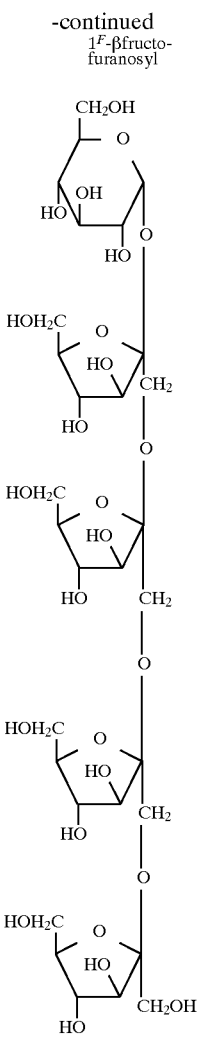

In general, the invention relates to a method of reducing the duration of diarrhea in a human, said method comprising enterally administering a therapeutically effective amount of an indigestible oligosaccharide to said human. The indigestible oligosaccharide is selected from the group consisting of fructooligosaccharides, fructosans, xylooligosaccharides and galactooligosaccharides having a DP of 2 to 20.

Methods and Materials

The indigestible oligosaccharides used in the clinical study were synthesized according to the method disclosed in U.S. Pat. No. 4,681,771 to Adachi et al. The teachings of U.S. Pat. No. 4,681,771 are incorporated herein by reference. The process comprises reacting sucrose in the presence of a fructosyltransferase from *Aspergillus niger* to obtain $GF_2$, $GF_3$, and $GF_4$.

The FOS used in the clinical study was obtained from Golden Technologies, Inc. of Westminster, CO. The Fructooligosaccharides Powder was Lot. No. 931115 and had the following chemical analysis:

| | |
|---|---|
| Moisture (w/w %) | 2.5 |
| Carbohydrate composition (% dry basis) | |
| Glucose and Fructose | 0.5 |
| Sucrose | 3.5 |
| FOS | 96.0 |
| $GF_2$ | 41.3 |
| $GF_3$ | 45.7 |
| $GF_4$ | 9.0 |

The Fructooligosaccharides Powder was a white powder with a granular size of less than 42 mesh. This FOS was used to prepare the milk-based fortified infant formula substantially in accordance with U.S. Pat. No. 5,021,245, the teachings of which are herein incorporated by reference. More specifically, to produce a 5,700 lb. batch of the powdered Experimental formula, a mixture of 20 lbs. of lactose, 110 lbs. of sucrose and 166 lbs. of FOS were dissolved in water. This carbohydrate solution was then combined with the protein, minerals, oils and vitamins set forth in Table 1, heat processed, homogenized, spray dried, and packaged into containers.

Study Design

A controlled blinded, randomized 16 week study of healthy children attending day care centers was conducted. Children between the ages of 10 and 24 months were enrolled in the study. The children were randomly assigned to be fed either a milk-based infant formula, which served as a Control, or an Experimental milk-based beverage supplemented with fructooligosaccharides (FOS). The study beverages were fed ad libitum as the child's sole source of milk beverages.

Upon entering into the study, children were placed under active surveillance for diarrhea and other significant medical illnesses. Evaluations were made at study day 7, 28, 56, 84 and 112. Research nurses visited the participating day care centers each week to ensure study compliance and identify episodes of diarrhea.

The primary outcome variables included incidence and duration of all diarrhea episodes.

Study Diet

The study beverages were powdered products that were reconstituted with water at the point of consumption. The powdered Control and Experimental beverages were reconstituted by mixing 135 grams of powdered nutritional with 1 liter of water. The beverages contained approximately 670 to 725 Kcal per liter. The powdered products were provided in clinically labeled 400 gram cans. The beverage was a modified, fortified milk-based drink with or without FOS that met the nutrient levels recommended by the Committee on Nutrition of the American Academy of Pediatrics as required by the Infant Formula Act of 1980. The study beverage compositions are shown in Table 1. Both beverages provided 20 calories per fluid ounce when reconstituted with water. The average daily intake for children receiving Control beverage was 750 mL and for children receiving Experimental beverage was 766 mL which resulted in consumption of approximately 2.6 grams of FOS per day.

TABLE 1

PRODUCT COMPOSITION
Approximate Composition of Study Beverage
With or Without Fructooligosaccharides (per liter)

| NUTRIENT | Experimental Study Beverage with Fructooligosaccharides | Control Study Beverage |
|---|---|---|
| Protein, g | 15.3 | 15.3 |
| Fat, g | 37.2 | 37.2 |

TABLE 1-continued

PRODUCT COMPOSITION
Approximate Composition of Study Beverage
With or Without Fructooligosaccharides (per liter)

| NUTRIENT | Experimental Study Beverage with Fructooligosaccharides | Control Study Beverage |
|---|---|---|
| Carbohydrate, g | 74.7 | 74.7 |
| Linolenic Acid, mg | 6500 | 6500 |
| Vitamin A, IU | 2900 | 2900 |
| Vitamin D, IU | 440 | 440 |
| Vitamin K, mcg | 112 | 112 |
| Thiamine ($B_1$), mcg | 239 | 239 |
| Riboflavin ($B_2$), mcg | 1505 | 1505 |
| Vitamin $B_{12}$, mcg | 3.24 | 3.24 |
| Niacin, mcg | 9000 | 9000 |
| Folic Acid (Folacin), mcg | 155 | 155 |
| Pantothenic Acid, mcg | 4250 | 4250 |
| Biotin, mcg | 45.0 | 45.0 |
| Vitamin C (Ascorbic Acid), mg | 150 | 150 |
| Choline, mg | 156 | 156 |
| Inositol, mg | 38 | 38 |
| Calcium, mg | 975 | 975 |
| Phosphorus, mg | 650 | 650 |
| Magnesium, mg | 75 | 75 |
| Iron, mg | 13 | 13 |
| Zinc, mg | 8.5 | 8.5 |
| Manganese, mcg | 52 | 52 |
| Copper, mcg | 710 | 710 |
| Sodium, mg | 220 | 220 |
| Iodine, mcg | 46 | 46 |
| Potassium, mg | 840 | 840 |
| Chloride, mg | 620 | 620 |
| Taurine, mg | 57.5 | 57.5 |
| Energy (Kcal) | 684 | 684 |
| β-Carotene, mcg | 400 | 400 |
| % Kcal from protein | 8.95 | 8.95 |
| Nucleotides, mg | 72 | 72 |
| FOS | 3.5 | 0 |

Study Subjects and Entry Procedures

Upon enrollment, study subjects were placed under continuous, active surveillance for diarrhea and other illnesses.

An initial assessment was made of each child attending the day care center. The children were in apparent good health with no clinical evidence of chronic gastroenteritis or diarrhea within seven days prior to enrollment; had no significant chronic or severe renal, liver or gastrointestinal tract function abnormalities; no history of aspiration pneumonia within 3 months prior to enrollment; and did not suffer from immune deficiency or receive immunosuppressive therapy. Children participating in another investigational drug study one month prior to enrollment were excluded from entering the study.

Children were prohibited from receiving human milk feedings for the duration of the study. All children had a history of ingesting whole cow's milk or cow's milk-based infant formula prior to enrollment and exhibited no symptoms of cow's milk allergy or cow's milk protein intolerance. Children were randomly assigned to receive the Control or the Experimental beverage.

Study Evaluations

Day care center records and clinic or physician visits were monitored for clinically significant illness: non-specific upper respiratory tract infections, bronchitis, bronchiolitis, bronchopneumonia, otitis media, diarrhea and other significant illnesses. Each subject was evaluated at entry, 7, 28, 56, 84 and 112 days (±3 days).

Diarrheal Episodes

Children were placed on active surveillance for diarrhea at enrollment and were followed through the 16 week study or until study exit. Parents and day care center workers were instructed to notify the research staff when a subject developed diarrhea. Diarrhea was defined as three watery or loose stools in a 24 hour period as determined by the parent, guardian, or day care center worker. Duration of diarrhea was the period in days from onset until the time of the last loose or watery stool. A diarrhea stool record was completed by the parent and day care center personnel. Diarrhea stool samples were collected for evaluation for rotavirus and other enteric pathogens and for *C. difficile* toxin. Specimens were collected within two (2) days of diarrhea onset. A recurrent episode of diarrhea is defined as diarrhea occurring at least 7 days after the end of a previous episode.

Statistical Methods

Duration of diarrhea was analyzed by the log rank test. For diarrhea duration outcomes, an analysis was performed for all episodes counted. In defining an episode of diarrhea, at least seven days must elapse between episodes of diarrhea or it is considered a single two-stage episode. The results are reported in Table 2.

TABLE 2

| EPISODES OF DIARRHEA | | |
|---|---|---|
| | EXPERIMENTAL N = 132 | CONTROL N = 135 |
| NUMBER OF CHILDREN WITH DIARRHEA | 40 | 45 |
| REPEAT EPISODES OF DIARRHEA | 3 | 11 |
| TOTAL NUMBER OF DIARRHEA EPISODES | 43 | 56 |

Duration of Diarrhea Episodes

The duration of diarrhea was determined by the number of days between first and last reported watery or loose stool. Repeat episodes and duration of diarrhea were shorter in subjects consuming Experimental. The mean duration of diarrhea was 3.91 days for children in the Experimental group and 4.88 days for children in the Control group. These data include duration of all diarrhea episodes occurring after eight days or more on the study regimen and meeting the protocol definition of three watery or loose stools in a twenty-four hour period. The difference in duration of diarrhea between the Experimental and Control groups is significant with a probability of p=0.036 using a marginal approach to Cox regression for clustered data. Data are summarized in Table 3.

TABLE 3

| DURATION OF DIARRHEA EPISODES | | |
|---|---|---|
| | Experimental | Control |
| NUMBER OF EPISODES | 43 | 56 |
| MEAN DURATION IN DAYS* | 3.91 | 4.88 |

*p = .036.

Repeat Episodes of Diarrhea

The number of repeat episodes of diarrhea was less in the Experimental than the Control group. These results indicate feeding FOS can decrease the number of recurrent episodes of diarrhea.

It is concluded from the results of the clinical study that administration of an indigestible oligosaccharide reduces the duration and number of recurrent episodes of diarrhea in children. Indigestible oligosaccharides, such as FOS, can be added to various nutritional products including but not limited to infant formula, milk-based and fruit-based products for older children and adults to accomplish the method of this invention. FOS may also be formulated in candies, lozenges, chewing gums, tablets and mixed into other food products.

Through the work of this investigation, it has been shown that the method of the present invention is efficacious and has been determined to be safe. The clinical trial proved the efficacy of the disclosed and claimed use of FOS in reducing the duration and recurrence of diarrhea. Differences where observed and support the present invention in reducing the duration and recurrence of diarrhea in children when taken as part of the daily diet. The prior art does not suggest or disclose that the prophylactic, enteral administration of FOS would be effective in reducing the duration of diarrhea.

Industrial Applicability

The results from the clinical study demonstrate that the method of this invention is effective in reducing the duration and recurrence of diarrhea. The medical community is constantly searching for methods and products that will be useful in the management of diarrhea and the present invention supplies a new approach to the control of this common problem.

While the methods and products wherein described constituted a preferred embodiment of this invention, it is understood that the invention is not limited to the precise method or formulation and that changes may be made therein without departing from the scope of the invention which is defined in the appended claims.

What is claimed is:

1. A method of reducing the duration of diarrhea in a human, said method comprises enterally administering nystose and $1^F$-β-fructofuranosyl nystose and mixtures thereof, on a prophylactic basis to said human in an amount effective to reduce the duration of diarrhea.

2. The method of claim 1 where said mixture of fructooligosaccharides is administered in a nutritional product.

3. The method of claim 2 wherein the nutritional product is an infant formula, follow-on formula, toddler's beverage, milk, yogurt, or fermented product.

4. The method of claim 2 wherein the nutritional product is an infant formula, follow-on formula, toddler's beverage, milk, yogurt, or fermented product.

5. The method of claim 1 wherein said mixture of fructooligosaccharides is administered in a candy a chewing gum, a tablet, a lozenge or a liquid.

6. The method of claim 1 wherein the mixture of fructooligosaccharides is administered at a rate of at least 0.5 grams per day to 5 grams per day.

7. A composition useful for reducing the duration of diarrhea, said composition comprising a mixture of nystose and $1^F$-β-fructofuranosyl nystose.

8. A method for reducing the duration of diarrhea in a human, said method comprises enterally administering to said human at least 0.5 grams per day of a mixture of fructooligosaccharides in which the fructooligosaccharide is selected from nystose and $1^F$-β-fructofuranosyl nystose and mixtures thereof.

* * * * *

(12) EX PARTE REEXAMINATION CERTIFICATE (9665th)
United States Patent
Dohnalek et al.

(10) Number: US 5,827,526 C1
(45) Certificate Issued: May 17, 2013

(54) USE OF INDIGESTIBLE OLIGOSACCHARIDES TO PREVENT GASTROINTESTINAL INFECTIONS AND REDUCE DURATION OF DIARRHEA IN HUMANS

(75) Inventors: Margaret Ione Halpin Dohnalek, Worthington, OH (US); Karin Margaret Ostrom, Reynoldsburg, OH (US); Milo Duane Hilty, Lewis Center, OH (US)

(73) Assignee: Abbott Laboratories, Abbott Park, IL (US)

Reexamination Request:
No. 90/012,204, Mar. 22, 2012

Reexamination Certificate for:
Patent No.: 5,827,526
Issued: Oct. 27, 1998
Appl. No.: 08/653,084
Filed: Jun. 12, 1996

Related U.S. Application Data

(60) Provisional application No. 60/001,036, filed on Jul. 11, 1995.

(51) Int. Cl.
| | | |
|---|---|---|
| *A61K 31/702* | (2006.01) | |
| *A61K 31/715* | (2006.01) | |
| *A23C 9/13* | (2006.01) | |
| *A23G 3/34* | (2006.01) | |
| *A23L 1/0528* | (2006.01) | |
| *A23L 2/52* | (2006.01) | |
| *A61K 31/733* | (2006.01) | |
| *A61P 1/12* | (2006.01) | |
| *A23L 1/052* | (2006.01) | |

(52) U.S. Cl.
USPC ........ 424/440; 424/439; 424/197.11; 424/73; 514/867; 514/54

(58) Field of Classification Search
None
See application file for complete search history.

(56) References Cited

To view the complete listing of prior art documents cited during the proceeding for Reexamination Control Number 90/012,204, please refer to the USPTO's public Patent Application Information Retrieval (PAIR) system under the Display References tab.

*Primary Examiner* — Evelyn Huang

(57) ABSTRACT

A method is provided for reducing the duration of diarrhea and recurrent episodes of diarrhea in humans by enterally administering indigestible oligosaccharides prophylactically. More specifically, the present invention relates to a method using indigestible oligosaccharides or fructooligosaccharides (FOS) to reduce the duration and recurrence of diarrhea in a human wherein between 0.5 grams and 5 grams of at least one FOS selected from the group consisting of 1-kestose, nystose, and $1^F$-$\beta$-fructofuranosyl nystose is administered to said human per day. The indigestible oligosaccharides can be produced through enzymatic synthesis, chemical techniques or isolated from plant materials and are administered in the form of a nutritional product, candy, tablets, chewing gum, lozenges, milk, yogurts, fermented products and the like.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-8 are cancelled.

\* \* \* \* \*